(12) United States Patent
Cardi et al.

(10) Patent No.: US 6,576,730 B2
(45) Date of Patent: Jun. 10, 2003

(54) ORGANIC INITIATORS AND THEIR USE IN THE POLYMERIZATION OF UNSATURATED MONOMERS

(75) Inventors: Nicoletta Cardi, Arona (IT); Riccardo Po', Leghorn (IT); Giuliana Schimperna, Novara (IT); Maria Caldararo, Trecate (IT); Maria Anna Cardaci, Marzano (IT); Fabio Garbassi, Novara (IT)

(73) Assignee: Enichem S.p.A., San Donato Milanese (IT)

( * ) Notice: Subject to any disclaimer, the term of this patent is extended or adjusted under 35 U.S.C. 154(b) by 162 days.

(21) Appl. No.: 09/852,697

(22) Filed: May 11, 2001

(65) Prior Publication Data

US 2002/0022724 A1 Feb. 21, 2002

(30) Foreign Application Priority Data

May 19, 2000 (IT) ................................. MI2000A001113

(51) Int. Cl.$^7$ .................................................. C08F 4/00
(52) U.S. Cl. ..................... 526/220; 526/310; 526/329.2; 526/346; 548/100; 540/1
(58) Field of Search ................................ 526/220, 346, 526/329.2, 310; 548/100; 540/1

(56) References Cited

U.S. PATENT DOCUMENTS 4,290,870 A  *  9/1981  Kondoh et al. ........ 204/159.15

* cited by examiner

Primary Examiner—David W. Wu
Assistant Examiner—William Cheung
(74) Attorney, Agent, or Firm—Oblon, Spivak, McClelland, Maier & Neustadt, P.C.

(57) ABSTRACT

Process for the polymerization of unsaturated vinyl and/or vinylidene monomers which comprises reacting one or more monomers in the presence of heterocyclic initiators having a nitrogen atom bound to an oxygen atom at a temperature ranging from 100 to 130° C.

17 Claims, No Drawings

ORGANIC INITIATORS AND THEIR USE IN THE POLYMERIZATION OF UNSATURATED MONOMERS

The present invention relates to a series of new groups of radicalic polymerization initiators of unsaturated vinyl and/or vinylidene monomers.

More specifically, the present invention relates to a new group of initiators for vinylaromatic monomers and their use in the radicalic polymerization thereof.

The initiators object of the present invention give the polymerization the characteristics of a "living" polymerization and therefore allow the production of block copolymers. With respect to the classical systems based on nitroxyl and peroxide radicals, they activate the polymerization of styrene at much lower temperatures (about 100° C.).

The polymerization of unsaturated monomers proceeds radicalically in the presence of suitable initiators, normally represented by peroxides (for example benzoyl peroxide, dicumyl peroxide, etc.) or by azo-compounds such as, for example, azobis(isobutyronitrile). In some cases, as in the case of styrene for example, the polymerization can be effected spontaneously by heating the monomer to over a certain temperature (100–110° C.), in correspondence with which there is the formation of particular adducts containing unpaired electrons which start the polymerization. In all these cases the polymerization is "non-living", i.e. the polymeric macroradical increases its molecular weight in a very short time and undergoes end or transfer reactions which cause the interruption of the chain. Other chains begin to form contemporaneously, due to the reaction with the initiator, which is characterized by its own half-life time and consequently continuously generates the radicalic species responsible for the polymerization over a period of time.

The result of this process is that it is impossible to control the molecular weights and, as a result of the end and transfer reactions, it is not possible to prepare block polymers, as is the case, on the contrary, with anionic polymerization. In this latter type of polymerization, called "living", there are practically no transfer or end reactions, and it is therefore possible to induce the growth of a block of a second monomer on a macromolecule. The polymeric chains, furthermore, all begin contemporaneously and grow at the same rate so that the end polymer has a very narrow molecular weight distribution and the molecular weight is exclusively determined by the monomer/initiator ratio, which can be pre-established as desired.

A series of initiator systems has recently been found, which are capable of also giving radicalic polymerization the characteristics of a "living" process. The use of iniferters is described in "Macromolecular Chemistry, Rapid Communication" 3, 127, 1982. These substances act as thermal and/or photochemical initiators as well as transfer agents and reversible chain-terminators; if they were not reversible they would fall into the category of classical radicalic polymerization. The iniferters specified are di-alkylthiouram disulfides, diaryl disulfides, etc. Monomers selected from methylmethacrylate, styrene, methylacrylate and vinylacetate are polymerized.

The disadvantages of this technique lie in the fact that both of the radicals produced by the decomposition of the initiator are capable of adding monomers and that there is limited industrial applicability owing to the use, in most cases, of UV radiation to initiate the process; in addition to this there are significant chain-termination reactions with a consequent loss in the polymerization life, as described in "Polymer Bulletin" (Berlin), 7, 197 1982).

Other examples of initiators are tetra-arylethanes which thermally decompose to give diphenyl alkyl radicals (Macromolecular Chemistry, 184, 745, 1983) and silylated pinacols (Journal of Polymer Science, Polymer Chemistry Ed, 24, 1251, 1986), but these systems are not very efficient and have therefore never been developed.

In U.S. Pat. No. 4,581,429 there is a first reference to the synthesis of homo and copolymers by means of the use of initiators of the $R_1R_2N$—O—X type (alkoxyamines) wherein $R_1$ and $R_2$ are substituents with no hydrogen in the carbon adjacent to the nitrogen atom, whereas X is a substituent of such a nature that the corresponding X radical, formed as a result of the thermal breakage of the NO-X bond, is capable of polymerizing unsaturated monomers by means of a radicalic mechanism. The chain growth control is due to the fact that the breakage reaction of the bond is an equilibrium reaction, and the nitroxy-radical formed is not capable of initiating the radicalic polymerization of the monomer. The use of alkoxyamines variously substituted and their synthesis is also described in Macromolecules, 28, 2993 (1995) and in Polymer Preprints, 40, 2, 315 (1999).

In U.S. Pat. No. 5,322,912, the alkoxyamine is generated directly in the reaction environment by mixing the stable nitroxy-radical, the peroxide and the monomer and heating to a suitable temperature.

U.S. Pat. Nos. 5,627,248 and 5,677,388 describe the use of bifunctional alkoxyamines having general formula $R_4R_5N$—O—$C(R_2R_3)$—$R_1$—$C(R_2R_3)$—O—$NR_4R_5$ in the radicalic polymerization process.

U.S. Pat. No. 5,910,549 describes a method for the preparation of alkoxyamines starting from nitroxy-radicals but in this, as in all previous cases, in the claims relating to the possible nitroxy-radicals or possible alkoxyamines, nitrogen and oxygen never form part of a cycle.

In international patent application WO 96/30421 a new process is proposed, consisting in the addition of a monomer to the growing radical generated by an alkyl halide by means of a reversible redox reaction catalyzed by transition metals such as Cu(I)/2bipyridyl. Polar monomers can be polymerized in this way, with the possibility of also obtaining block and grafted copolymers. One of the disadvantages of this technology is associated with the metallic residue in the synthesized material which can cause degradation of the chains undergoing transformation, and also the production of low molecular weights.

Polym. Prep., 35(1), 704 (1994) describes the use of cobalt porphyrins as controllers in the polymerization of methacrylates; although these systems produce polymers with high molecular weights and a low polydispersity, they have a high cost and, if not supported and therefore filtered, give the polymer an undesired colouring.

International patent application WO 98/01478 describes a new living radicalic polymerization method called RAFT (Reversible Addition-Fragmentation Transfer) in which thio-esters having general formula S=C(Z)SR are used as transfer agents. Acrylic monomers are also polymerized with this technique, but their release may cause problems relating to bad smell and undesired colouring of the polymer, owing to the low molecular weight of the sulfurized compounds.

The Applicant has now identified a new category of initiators active in the polymerization of unsaturated monomers, in particular vinylaromatic monomers, which have the additional advantage of allowing the formation of block structures. These initiators are already active at temperatures of 100° C. and are thermally activated without having to resort to the use of particular radiation sources, which distinguishes them from previously known systems. Furthermore, unlike the systems based on the combination of peroxides or azo-compounds with nitroxyl radicals, they are "monocomponent", which greatly facilitates dosage in the reaction phase.

An object of the present invention therefore relates to organic initiators for the polymerization of unsaturated vinyl and/or vinylidene monomers characterized by the presence of a heterocyclic structure having a nitrogen atom bound to an oxygen atom in the same cycle and having the general formula selected from structures (I)-(X) illustrated below.

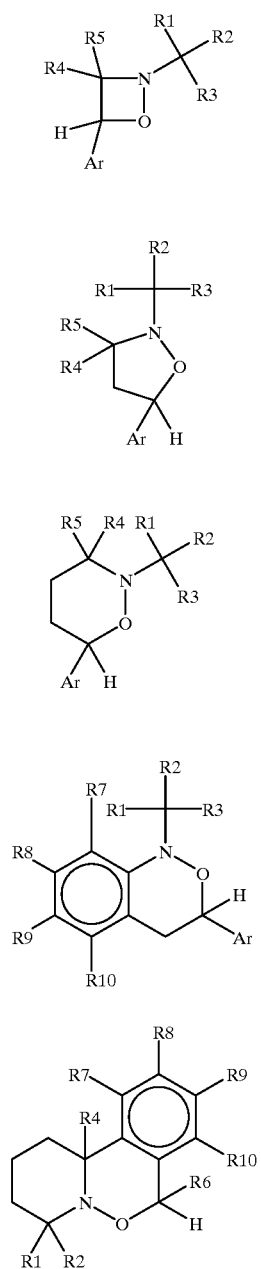

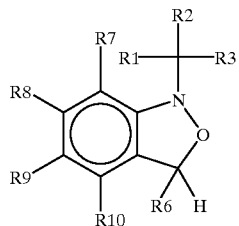

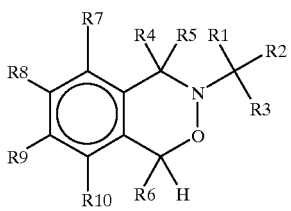

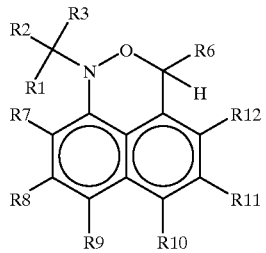

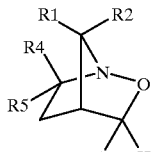

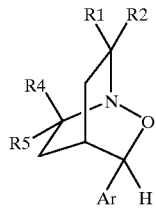

wherein only one of R1, R2, R3, R4, R5 is hydrogen, whereas the remaining are a linear or branched $C_1$–$C_6$ alkyl radical, or $C_6$–$C_{12}$ aryl radical, if one of R4 or R5 is hydrogen then the remaining R4 or R5 is an aryl radical, if one of R1 or R2 or R3 is hydrogen then one and only one of the remaining R1 or R2 or R3 is an aryl radical; R6 represents a hydrogen atom or a linear or branched $C_1$–$C_6$ alkyl radical, or a —$CH_2$—R14 group, wherein R14 represents a $C_1$–$C_6$ alkyl radical, $C_6$–$C_{12}$ aryl or $C_7$–$C_{15}$ alkylaryl radical; Ar is a phenyl which can contain substituents on the aromatic ring represented by halogens, linear or branched $C_1$–$C_6$ alkyl groups, carboxyl groups; R7–R13 independently represent a halogen, such as chlorine, or a hydrogen atom or are selected from $C_1$–$C_6$ alkyl groups, optionally halogenated, $C_6$–$C_{12}$ aryl groups, carboxyl, alkoxyl or acyl groups containing from 1 to 15 carbon atoms, sulfonic, phosphonic, phosphinic, amine, amide, nitric groups containing up to 15 carbon atoms.

Examples of products according to the group having general formula (I) are:
2-(1,1-dimethylethyl)-3-ethyl-4-phenyl-1,2 oxazethidine;
2-(1,1-dimethylethyl)-3-methyl-4-phenyl-1,2 oxazethidine;
2-(1,1-dimethylethyl)-3,3-dimethyl-4-phenyl-1,2oxazethidine;
2-(1,1-dimethylethyl)-3,4-diphenyl-1,2 oxazethidine.

Examples of products according to group (II) are:
2-(1,1-dimethylethyl)-3,3-dimethyl-5-phenyl-isoxazolidine;
2-(1,1-dimethylethyl)-3,5-diphenyl-isoxazolidine;
2-(1-methylethyl)-3,3-dimethyl-5-phenyl-isoxazolidine;
2-(1,1-dimethylethyl)-3,3-dimethyl-5(4-methoxyphenyl)-isoxazolidine;
2-(1,1-dimethylethyl)-3,3-dimethyl-5(4-chlorophenyl)-isoxazolidine;
2-(1,1-dimethylethyl)-3,3-dimethyl-5(2,4-dimethoxyphenyl)-isoxazolidine.

Examples of products according to group (III) are:
2-(1,1-dimethylethyl)-3,3-dimethyl-6-phenyl-2H-3,4-dihydro-5,6-dihydro-1,2-oxazine;
2-(1,1-dimethylethyl)-3,6-diphenyl-2H-3,4-dihydro-5,6-dihydro-1,2-oxazine;
2-(1-methylethyl)-3,3-dimethyl-6-phenyl-2H-3,4-dihydro-5,6-dihydro-1,2-oxazine;
2-(1,1-dimethylethyl)-3,3-dimethyl-6(4-methoxyphenyl)-2H-3,4-dihydro-5,6-dihydro-1,2-oxazine;
2-(1,1-dimethylethyl)-3,3-dimethyl-6(2,4-dimethoxyphenyl)-2H-3,4-dihydro-5,6-dihydro-1,2-oxazine;
2-(1,1-dimethylethyl)-3,3-dimethyl-6(4-chlorophenyl)-2H-3,4-dihydro-5,6-dihydro-1,2-oxazine.

Examples of products according to group (IV) are:
1-(1,1-dimethylethyl)-3-phenyl-1H-3,4-dihydro-2,1-benzoxazine;
1-(1,1-dimethylethyl)-3-phenyl-5-methyl-1H-3,4-dihydro-2,1-benzoxazine;
1-(1,1-dimethylethyl)-3-phenyl-5,8-dimethoxy-1H-3,4-dihydro-2,1-benzoxazine;
1-(1,1-dimethylethyl)-3-phenyl-6,7-dimethoxy-1H-3,4-dihydro-2,1-benzoxazine;
1-(1,1-dimethylethyl)-3-phenyl-5,8-dichloro-1H-3,4-dihydro-2,1-benzoxazine.

An example of a product having general formula (V) is:
1,2,3,4-tetrahydro-7H-11bH-pyrido[2,1-d][2,3]benzoxazine.

Examples of products according to group (VI) are:
1-(1,1-dimethylethyl)-3-ethyl-1H-3H-2,1-benzoxazole;
1-(1,1-dimethylethyl)-3-methyl-5-methoxy-1H-3H-2,1-benzoxazole;
1-(1,1-dimethylethyl)-3-propyl-4,7-dimethyl-1H-3H-2,1-benzoxazole;
1-(1-methylethyl)-3-ethyl-1H-3H-2,1-benzoxazole.

Examples of products according to group (VII) are:
1,4,4-trimethyl-3(1,1-dimethylethyl)-1H-3,4-dihydro-2,3-benzoxazine;
1,4,4-trimethyl-3(1-methylethyl)-1H-3,4-dihydro-2,3-benzoxazine;
1,4,4-trimethyl-3(1,1-dimethylethyl)-5-methoxy-1H-3,4-dihydro-2,3-benzoxazine;
1,4,4-trimethyl-3(1,1-dimethylethyl)-5,8-dichloro-1H-3,4-dihydro-2,3-benzoxazine;

An example of a product having general formula (VIII) is:
1-(1,1dimethylethyl)-1-aza-2-oxa-3H-phentalene.

Examples of products according to group (IX) are:
3-phenyl-2-oxa-6,6-dimethyl-1-azabicyclo [2.2.1] heptane;
3(4-methoxyphenyl)-2-oxa-6,6-dimethyl-1-azabicyclo [2.2.1] heptane;
3,6-diphenyl-2-oxa-6,6-dimethyl-1-azabicyclo [2.2.1] heptane;
3-phenyl-2-oxa-6,6-diethyl-1-azabicyclo [2.2.1] heptane;

Examples of products according to group (X) are:
3-phenyl-2-oxa-6,6-dimethyl-1-azabicyclo [2.2.2] octane;
3(4-methoxyphenyl)-2-oxa-6,6-dimethyl-1-azabicyclo [2.2.2] octane;
3,6-diphenyl-2-oxa-6,6-dimethyl-1-azabicyclo [2.2.2] octane;
3-phenyl-2-oxa-6,6-diethyl-1-azabicyclo [2.2.2] octane.

A further object of the present invention relates to a process for the polymerization of vinylaromatic monomers which comprises reacting at least one vinylaromatic monomer in the presence of one or more initiators having general formulae (I)–(X).

The term vinylaromatic monomers as used in the present description and claims mainly refers to styrene but can also refer to other styrene monomers having one or more hydrogen atoms substituted with $C_1$–$C_4$ alkyl or aryl radicals, a halogen or a nitro radical such as, for example, methylstyrene, vinylnaphthalene, mono-, di-, tri-, tetra-, pentachloro styrene, styrenes alkylated in the nucleus such as ortho-meta- and para-methylstyrene, ortho-meta- and para-ethylstyrene, etc., either alone or mixed with each other and/or with styrene.

The vinylaromatic monomer can be used in a mixture with an ethylenically unsaturated nitrile such as acrylonitrile or methacrylonitrile, for example in a quantity ranging from 0.1 to 50% by weight with respect to the total monomers, or, as an alternative to or in addition to ethylenically unsaturated nitrile, mixed with other ethylenically unsaturated monomers in such quantities that the vinylaromatic monomer is present in a concentration higher than 40% by weight.

Examples of ethylenically unsaturated monomers are alkyl or cycloalkyl esters of acrylic or methacrylic acid in which the alkyl or cycloalkyl groups contain from 1 to 4 carbon atoms and from 4 to 10 carbon atoms respectively, such as methylacrylate, methylmethacrylate, ethylacrylate, ethylmethacrylate, butylmethacrylate, cyclohexylmethacrylate, etc. Another ethylenically unsaturated monomer can be maleic anhydride.

Block copolymers can also be prepared by the polymerization of the first monomer or mixture of monomers up to a conversion ranging from 5 to 99% and subsequent feeding of the second monomer or mixture of monomers. The first copolymer block can be isolated by precipitation in a non-solvent and subsequently re-copolymerized by dissolution in the monomer or mixture of monomers forming the second copolymer block.

An inert solvent, which acts as diluent, is added to the mixture to be polymerized in a quantity not higher than 20% and preferably from 1 to 15% by weight, with respect to the mixture to be polymerized. Examples of suitable inert solvents are aromatic hydrocarbons such as ethylbenzene, ketones, esters and nitriles which are liquid at the polymerization temperature. In addition to the ethylbenzene mentioned above, toluene, xylenes or their mixtures, can be used, as aromatic hydrocarbons. Examples of ketones are 2-butanone, methylethylketone, cyclohexanone, etc. Other examples of solvents particularly suitable for the present process are ethyl acetate and acetonitrile.

The polymerization reaction is substantially carried out under the same conditions as the traditional peroxide polymerization, except for the reaction temperature which ranges from 100 to 130° C., preferably below 120° C. The polymerization can be carried out in the presence of water.

Some illustrative but non-limiting examples are provided for a better understanding of the present invention and for its embodiment.

EXAMPLE 1

Synthesis of 1-(1,1-dimethylethyl)-3-methyl-1H-3H-2,1-benzoxazole

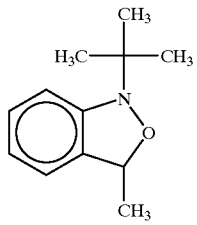

Synthesis of the Intermediate A:

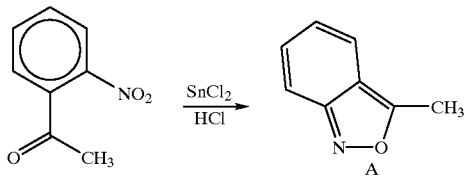

o-nitroacetophenone=10 g (60.6 mmoles)
Tin chloride=41 g (216.9 mmoles)
Concentrated hydrochloric acid=105 cc The tin chloride and concentrated hydrochloric acid are charged. The mass is cooled to 10° C. and nitroacetophenone is slowly added dropwise.

At the end of the addition, the mixture is stirred at room temperature for 2 hours. After this period the reaction is complete upon TLC control.

Water and ice are added to the reaction raw product, the organic phase is then extracted with ethyl ether. The joined ether extracts are washed with a diluted aqueous solution of sodium bicarbonate and then with water until neutrality and anhydrified on sodium sulfate, the solvent being removed by evaporation at reduced pressure. 7.4 g of intermediate A (unitary upon TLC). Yield 82%.

b) Synthesis of Intermediate B

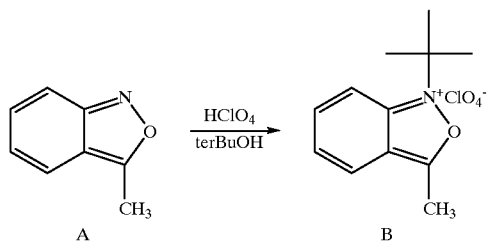

Intermediate A=7.4 g (50 mmoles)
nitromethane=150 cc
t-butanol=5.8 cc (55 mmoles)
perchloric acid 70%=4.9 cc (78.4 mmoles)

The reagents are charged in the order described and the mixture is left under stirring at 20° C. for 24 hours. TLC control confirms the disappearance of the starting product.

Ethyl ether is added to the reaction raw product and the desired perchlorate precipitates. The precipitate is filtered, subsequently dissolved in acetone and re-precipitated with ethyl ether. 14 g of intermediate B (white solid) are obtained. Yield 92%.

c) Synthesis of 1-(1,1-dimethylethyl)-3-methyl-1H-3H-2,1-benzoxazole According to the Following Scheme:

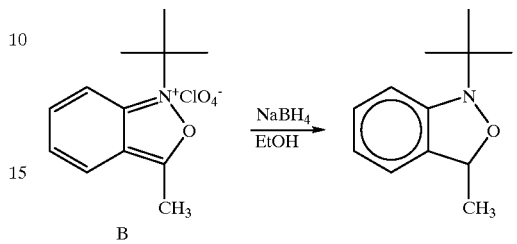

Intermediate B=14 g (46 mmoles)
Sodium borohydride=2 g (52.6 mmoles)
Ethanol=100 cc The perchlorate and ethanol are charged and the sodium borohydride is then added in small portions. At the end of the addition the mixture is left under stirring at room temperature for 30 minutes.

Water is carefully added to the reaction raw product, an oily product is separated.

The ethanol is evaporated and the product is extracted with ethyl ether. 7.4 g of product are obtained. The product is purified on a silica gel chromatographic column (eluant: hexane/ethyl acetate 99:1). The product was characterized by means of $^1$H NMR: (200 MHz, CDCl$_3$) δ (ppm): 1.3 (9H, s); 1.5 (3H, d); 5.58 (1H, q); 6.9–7.2 (4H).

EXAMPLE 2

20 ml of styrene (175 mmoles) deaerated by nitrogen bubbling and 11.5 mg of 1-(1,1-dimethylethyl)-3-methyl-1H-3H-2,1-benzoxazole (0.0603 mmoles) dissolved in 1.5 ml of ethylbenzene were charged into a 50 ml test-tube.

The reaction mixture was heated to 125° C. for 5 hours. Samples of the reaction mixture were removed at 1 hour intervals to determine the conversion and molecular weight.

The isolation of the polymer was effected by means of precipitation in an excess of ethanol, filtration and drying at 60° C. Table 1 below indicates the conversions measured and Mn values.

TABLE 1

| Time (h) | Conversion (w %) | Mn |
| --- | --- | --- |
| 1 | 15 | 138,000 |
| 2 | 28 | 155,000 |
| 3 | 39 | 143,000 |
| 4 | 57 | 159,000 |
| 5 | 65 | 153,000 |

EXAMPLE 2 (COMPARATIVE)

The procedure of example 2 was repeated using 9.4 mg of 2,2,6,6-tetramethylpiperidinyloxyl (0.0603 mmoles) and 15 mg of benzoyl peroxide at 75% (0.046 mmoles) instead of 1-(1,1-dimethylethyl)-3-methyl-1H-3H-2,1-benzoxazole. Samples of the reaction mixture were removed at intervals of 1.5 hours to determine the conversion and molecular weight.

The isolation of the polymer was effected by means of precipitation in an excess of ethanol, filtration and drying at 60° C. The conversion and Mn data are indicated in Table 2.

TABLE 2

| Time (h) | Conversion (w %) | Mn |
|---|---|---|
| 1.5 | 25 | 38,400 |
| 3 | 42 | 54,500 |
| 4.5 | 55 | 67,100 |
| 6 | 72 | 67,300 |

EXAMPLE 3

30 ml of styrene (262 mmoles) deaerated by nitrogen bubbling and 17.3 mg of 1-(1,1-dimethylethyl)-3-methyl-1H-3H-2,1-benzoxazole dissolved in 2.25 ml of ethylbenzene were charged into a 100 ml test-tube.

The reaction mixture was heated to 110° C. for 6 hours.

The isolation of the polymer was effected by means of precipitation in an excess of ethanol, filtration and drying at 60° C. 7.75 g of polystyrene were obtained, equal to a conversion of 28%.

EXAMPLE 3 (COMPARATIVE)

The procedure of example 3 was repeated using 14.1 mg of 2,2,6,6-tetramethylpiperidinyloxyl (0.0945 mmoles) and 22.5 mg of benzoyl peroxide at 75% (0.069 mmoles) instead of 1-(1,1-dimethylethyl)-3-methyl-1H-3H-2,1-benzoxazole. At the end of 6 hours no polymeric product was obtained.

EXAMPLE 4

20 ml of styrene (175 mmoles) deaerated by nitrogen bubbling and 11.5 mg of 1-(1,1-dimethylethyl)-3-methyl-1H-3H-2,1-benzoxazole (0.0603 mmoles) dissolved in 1.5 ml of ethylbenzene were charged into a 50 ml test-tube.

The reaction mixture was heated to 100° C. for 4 hours. Samples of the reaction mixture were removed at 1 hour intervals to determine the conversion and molecular weight.

The isolation of the polymer was effected by means of precipitation in an excess of ethanol, filtration and drying at 60° C. The conversion data are indicated in Table 3.

TABLE 3

| Time (h) | Conversion (w %) | Mn |
|---|---|---|
| 1 | 2.8 | 99,000 |
| 2 | 5.6 | 149,000 |
| 3 | 9.0 | 197,000 |
| 4 | 12 | 203,000 |

EXAMPLE 4 (COMPARATIVE)

The procedure of example 4 was repeated using 9.4 mg of 2,2,6,6-tetramethylpiperidinyloxyl (0.0603 mmoles) and 15 mg of benzoyl peroxide at 75% (0.046 mmoles) instead of 1-(1,1-dimethylethyl)-3-methyl-1H-3H-2,1-benzoxazole. At the end of 4 hours no polymeric product was obtained. The reaction was continued for a further two hours without obtaining any product.

EXAMPLE 5

1.505 g of polystyrene prepared with an analogous procedure to that described in example 2 (4.5 hours of reaction), 13.4 ml of styrene (117 mmoles) and 4.7 ml of acrylonitrile (71 mmoles), both deaerated by means of prolonged nitrogen bubbling, were charged into a 50 ml glass reactor. The mixture was reacted for 1 hour at 125° C.

The end-product was recovered by means of precipitation in a large excess of ethanol, filtration and drying in an oven at 60° C. 5.52 g of polymeric product were obtained which, upon chromatographic analysis, proved to have a peak which could be attributed to the presence of polystyrene block copolymer/styrene-acrylonitrile copolymer.

EXAMPLE 6

1.502 g of polystyrene prepared in example 3, 13.4 ml of styrene (117 mmoles) and 4.7 ml of acrylonitrile (71 mmoles), both deaerated by means of prolonged nitrogen bubbling, were charged into a 50 ml glass reactor. The mixture was reacted for 1 hour at 110° C. The end-product was recovered by means of precipitation in a large excess of ethanol, filtration and drying in an oven at 60° C.

2.74 g of polymeric product were obtained which, upon chromatographic analysis, proved to have a peak which could be attributed to the presence of polystyrene block copolymer/styrene-acrylonitrile copolymer.

EXAMPLE 7

Synthesis of 2-(1,1-dimethylethyl)3,3-dimethyl-5-phenyl-isoxazolidine

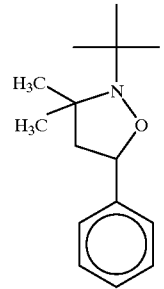

a) Synthesis of the Intermediate C:

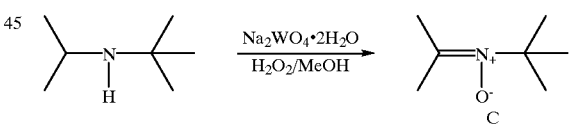

N-(1,1-dimethylethyl)isopropylamine=1.1 g (19.98 mmoles)
Sodium tungstate dihydrate=264 mg (0.8 mmoles)
Hydrogen peroxide 35%=5 cc (60 mmoles)
Methanol=20 cc All the reagents are charged except for the hydrogen peroxide which is slowly added dropwise after cooling the reaction mass to 0° C. At the end of the addition the mixture is left to spontaneously rise to room temperature. After 3 hours, the reaction is complete. Upon TLC, the unitary desired product is obtained.

Ethyl ether is added to the reaction raw product, the reactor is cooled to 0° C. and a saturated solution of sodium sulfite is slowly added dropwise.

The phases are separated, the organic phase is washed to neutrality with a saturated solution of NaCl and anhydrified with sodium sulfate and the solvent is evaporated at reduced pressure. 1.2 g of the desired intermediate C are obtained, in a quantitative yield.

b) Synthesis of 2-(1,1-dimethylethyl)-3,3-dimethyl-5-phenyl-isoxazolidine:

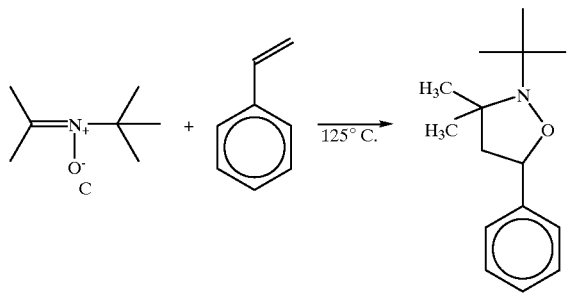

Intermediate C=1 g (7.75 mmoles)
Styrene=3.3 cc

The reagents are charged into an autoclave and the temperature is brought to 125° C. The mixture is left under stirring for 8 hours.

Gaschromatographic (GC) and TLC control confirms the disappearance of the starting nitron and the formation of the desired product. The residual styrene is completely removed at reduced pressure. The raw product obtained is purified on a silica gel column (eluant: hexane/ethyl acetate 9:1).

The product was characterized by means of $^1$H NMR: (200 MHz, CDCl$_3$) δ (ppm): 7.3 (5H, m); 4.9 (1H, t); 2.45 (1H, dd); 2.1 (1H, dd); 1.39 (3H, s); 1.35 (3H, s); 1.3 (9H, s).

EXAMPLE 8

12.8 ml of styrene (112 mmoles) deaerated by nitrogen bubbling and 9 mg of 2-(1,1-dimethylethyl)-3,3-dimethyl-5-phenyl-oxazolidine (0.0386 mmoles) dissolved in 1 ml of ethylbenzene were charged into a 50 ml test-tube. The reaction mixture was heated to 125° C. for 6 hours.

Samples of the reaction mixture were removed at 1.5 hour intervals to determine the conversion and molecular weight. The isolation of the polymer was effected by means of precipitation in an excess of ethanol, filtration and drying at 60° C.

The conversion and Mn data are indicated in Table 4.

TABLE 4

| Time (h) | Conversion (w %) | Mn |
|---|---|---|
| 1.5 | 22 | 131,000 |
| 3 | 44 | 139,000 |
| 4.5 | 60 | 147,000 |
| 6 | 69 | 156,000 |

EXAMPLE 9

12.8 ml of styrene (112 mmoles) deaerated by nitrogen bubbling and 9 mg of 2-(1,1-dimethylethyl)-3,3-dimethyl-5-phenyl-oxazolidine (0.0386 mmoles) dissolved in 1 ml of ethylbenzene were charged into a 50 ml test-tube. The reaction mixture was heated to 110° C. for 4.5 hours.

Samples of the reaction mixture were removed at 1.5 hour intervals to determine the conversion and molecular weight. The isolation of the polymer was effected by means of precipitation in an excess of ethanol, filtration and drying at 60° C.

The conversion and Mn data are indicated in Table 5.

TABLE 5

| Time (h) | Conversion (w %) | Mn |
|---|---|---|
| 1.5 | 7.4 | 72,200 |
| 3 | 15 | 83,200 |
| 4.5 | 23 | 133,000 |

EXAMPLE 10

1.002 g of polystyrene prepared according to the procedure described in example 9 together with 8.9 ml of styrene (78 mmoles) and 3.1 ml of acrylonitrile (47 mmoles), both deaerated by means of prolonged nitrogen bubbling, were charged into a 50 ml glass reactor. The mixture was reacted for 1 hour at 110° C.

The end-product was recovered by means of precipitation in a large excess of ethanol, filtration and drying in an oven at 60° C.

1.513 g of polymeric product were obtained which, upon chromatographic analysis, proved to have a peak which could be attributed to the presence of polystyrene block copolymer/styrene-acrylonitrile copolymer.

EXAMPLE 11

Synthesis of 1-(1,1-diemthylethyl)-3-methyl-4,7-dimethoxy-1H-3H-2,1-benzoxazole.

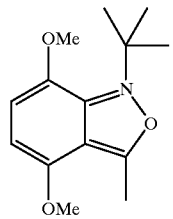

Synthesis of Intermediate D

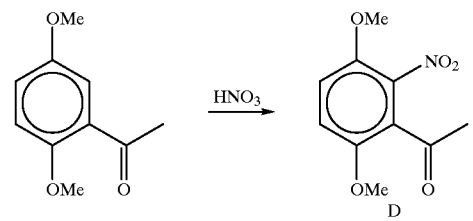

8.0 g (44.4 mmoles) of 2,5-dimethoxy acetophenone
40 ml of nitric acid (65%)

The 2,5-dimethoxy acetophenone is slowly added dropwise the nitric acid, at −20° C. 5 minutes after the end of the dripping, the reaction mass is poured into ice. The precipitate is filtered and washed with water. The precipitate is dissolved inn ethyl ether and washed to neutrality with water. After anhydrifying the organic phase on sodium sulfate, the solvent is removed by evaporation under vacuum.

6.0 g of intermediate D (yield=60%) are obtained, after purification on a chromatographic column (SiO$_2$; eluant: hexane/ethyl acetate=1/1).

Synthesis of Intermediate E

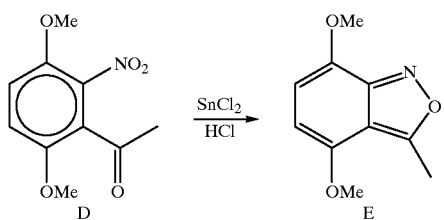

1.0 g (4.44 mmoles) intermediate D
3.0 g (15.8 mmoles) tin(II)chloride
10 ml hydrochloric acid (37%)

Intermediate D is added, in portions at 10° C., to the mixture of tin(II)chloride in concentrate hydrochloric acid. The temperature is brought to 20° C. After 3 hours ice is added to the reaction mixture and the product is extracted with ethyl ether. The organic extracts are washed to neutrality first with a saturated aqueous solution of sodium bicarbonate and finally with water. After anhydrifying the organic extracts, the solvent is removed by evaporation at reduced pressure. 0.7 g of product are thus obtained (yield=75%).

Synthesis of Intermediate F:

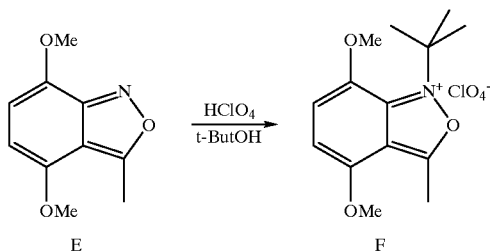

0.7 g (3.34 mmoles) intermediate E
0.389 ml (3.67 mmoles) terbutanol
0.329 ml (3.67 mmoles) perchloric acid
14 ml nitromethane Terbutanol and perchloric acid are added in order to the solution of intermediate E in nitromethane. After 20 hours, the product precipitates by the addition of ethyl ether, and is isolated by filtration. The product is purified by dissolution in acetone and precipitation with ethyl ether. It is filtered and washed several times with ethyl ether. 600 mg of product are thus obtained (yield=49%). Synthesis of 1-(1,1-dimethylethyl)-3-methyl-4,7-dimethoxy-1H-3H-2,1-benzoxazole

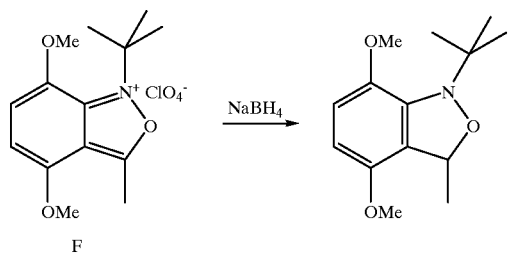

600 mg (1.6 mmoles) intermediate F
75 mg (1.9 mmoles) sodium borohydride
10 ml ethanol The sodium borohydride is added in portions to the suspension of intermediate F in ethyl alcohol. After 2 hours, water is added and, after removing the ethanol by evaporation under vacuum, the desired product precipitates and is isolated by filtration. The precipitate is washed several times with water until neutrality. 328 mg of product are thus obtained (yield=82%).

EXAMPLE 12

20 ml of styrene (175 mmoles) deaerated by nitrogen bubbling and 15.0 mg of 1-(1,1-dimethylethyl)-3-methyl-4,7-dimethoxy-1H-3H-2,1-benzoxazole dissolved in 1.5 ml of ethylbenzene were charged into a 50 ml test-tube.

The reaction mixture was heated to 110° C. for 6 hours.

The isolation of the polymer was effected by means of precipitation in an excess of ethanol, filtration and drying at 60° C.

The conversion and Mn data are indicated in Table 6.

TABLE 6

| Time (h) | Conversion (w %) | Mn |
|---|---|---|
| 2 | 5 | 45,371 |
| 3 | 9.7 | 48,841 |
| 4 | 19 | 60,997 |
| 6 | 37 | 63,181 |

EXAMPLE 13

20 ml of styrene (175 mmoles) deaerated by nitrogen bubbling and 15.0 mg of 1-(1,1-dimethylethyl)-3-methyl-4,7-dimethoxy-1H-3H-2,1-benzoxazole dissolved in 1.5 ml of ethylbenzene were charged into a 50 ml test-tube.

The reaction mixture was heated to 125° C. for 4 hours.

The isolation of the polymer was effected by means of precipitation in an excess of ethanol, filtration and drying at 60° C.

The conversion and Mn data are indicated in Table 7.

TABLE 7

| Time (h) | Conversion (w %) | Mn |
|---|---|---|
| 1 | 13 | 133,000 |
| 2 | 25 | 141,000 |
| 3 | 37 | 148,000 |
| 4 | 48 | 154,000 |

EXAMPLE 14

0.5 g of polystyrene prepared according to the procedure described in example 12 together with 4 ml of styrene (34 mmoles) and 1.5 ml of acrylonitrile (22.6 mmoles), both deaerated by means of prolonged nitrogen bubbling, were charged into a 50 ml glass reactor. The mixture was reacted for 1 hour at 125° C.

The end-product was recovered by means of precipitation in a large excess of ethanol, filtration and drying in an oven at 60° C. 2.12 g of polymeric product were obtained which, upon chromatographic analysis, proved to have a peak which could be attributed to the presence of polystyrene block copolymer/styrene-acrylonitrile copolymer.

What is claimed is:

1. A compound of the formula:

(I) 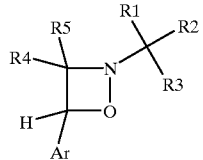

(II) 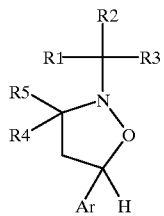

(III) 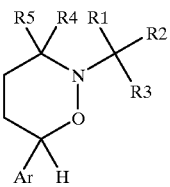

(IV) 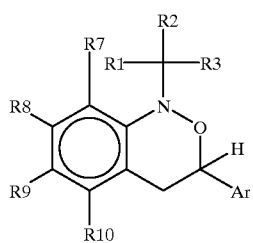

(V) 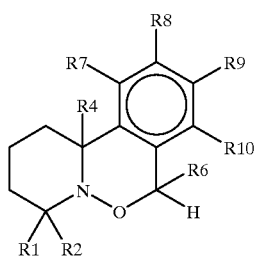

(VI) 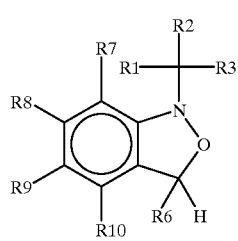

(VII) 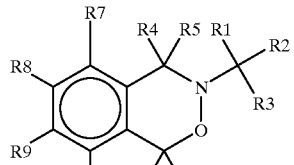

(VIII) 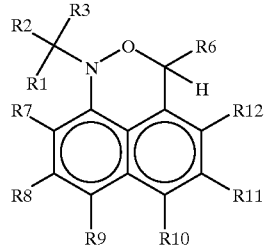

(IX) 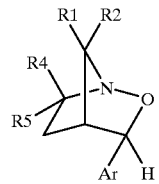

(X) 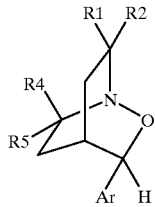

wherein only one of R1, R2, R3, R4, R5 is hydrogen, whereas the remaining are a linear or branched $C_1$–$C_6$ alkyl radical, or $C_6$–$C_{12}$ aryl radical, if one of R4 or R5 is hydrogen then the remaining R4 or R5 is an aryl radical, if one of R1, R2, or R3 is hydrogen then only one of the remaining R1, R2, or R3 is an aryl radical;

R6 represents a hydrogen atom, a linear or branched $C_1$–$C_6$ alkyl radical, or a —$CH_2$–R14 group, wherein R14 represents a $C_1$–$C_6$ alkyl radical, $C_6$–$C_{12}$ aryl or $C_7$–$C_{15}$ alkylaryl radical; Ar is a phenyl radical which can contain substituents on the aromatic ring represented by halogens, linear or branched $C_1$–$C_6$ alkyl groups, or carboxyl groups; R7–R12 independently represent a halogen, or a hydrogen atom or are selected from $C_1$–$C_6$ alkyl groups, optionally halgenated, $C_6$–$C_{12}$ aryl groups, carboxyl, alkoxyl or acyl groups containing from 1 to 15 carbon atoms, sulfonic, phosphonic, phosphinic, amine, amide, or nitric groups containing up to 15 carbon atoms.

2. A process for the polymerization of vinylaromatic monomers which comprises reacting at least one vinylaromatic monomer in the presence of one or more of compounds formulae (I)–(X) as defined in claim 1.

3. The process according to claim 2, wherein the vinylaromatic monomer is used in a mixture with an ethylenically unsaturated nitrile in quantities ranging from 0.1 to 50% by weight with respect to the total monomers, or, as an alternative to or in addition to the ethylenically unsaturated nitrile, in a mixture with other ethylenically unsaturated monomers in such quantities that the vinylaromatic monomer is present in a concentration higher than 40% by weight.

4. The process according to claim 2 for the preparation of block copolymers by means of the polymerization of the first monomer or mixture of monomers up to a conversion ranging from 5 to 99% and subsequent feeding of the second monomer or mixture of monomers.

5. The process according to claim 2, wherein an inert solvent is added to the mixture to be polymerized in a quantity not higher than 20% by weight with respect to the mixture itself.

6. The process according to claim 2, wherein the polymerization is substantially carried out at a temperature ranging from 100 to 130° C.

7. A compound according to claim 1, wherein the halogen of R7–R13 is chlorine.

8. A compound according to claim 1 of the Formula (I).

9. A compound according to claim 1 of the Formula (II).

10. A compound according to claim 1 of the Formula (III).

11. A compound according to claim 1 of the Formula (IV).

12. A compound according to claim 1 of the Formula (V).

13. A compound according to claim 1 of the Formula (VI).

14. A compound according to claim 1 of the Formula (VII).

15. A compound according to claim 1 of the Formula (VIII).

16. A compound according to claim 1 of the Formula (IX).

17. A compound according to claim 1 of the Formula (X).

* * * * *